United States Patent [19]

Aquino

[11] 4,383,615

[45] May 17, 1983

[54] SYRINGE TRAY

[75] Inventor: Richard A. Aquino, Gurnee, Ill.

[73] Assignee: Sherwood Medical Company, St. Louis, Mo.

[21] Appl. No.: 201,889

[22] Filed: Oct. 30, 1980

[51] Int. Cl.³ .............................................. A47F 7/00
[52] U.S. Cl. .................................. 211/60 R; 206/366; 211/78
[58] Field of Search ...................... 211/60 R, 60 A, 70, 211/78, 131; 206/365, 366, 564, 443; 422/104

[56] References Cited

U.S. PATENT DOCUMENTS

| | | | |
|---|---|---|---|
| 2,131,807 | 10/1938 | Jerum | 211/70 X |
| 2,313,905 | 3/1943 | Wallin | 211/60 R |
| 2,835,377 | 5/1958 | May et al. | 206/366 |
| 2,929,510 | 3/1960 | Penn | 211/60 R |
| 3,207,302 | 9/1965 | Hobbs | 206/366 |
| 3,261,660 | 7/1966 | Wilkinson | 211/60 R X |
| 3,305,084 | 2/1967 | Higgins et al. | 206/366 |
| 3,351,210 | 11/1967 | Murcott | 211/74 |
| 3,642,123 | 2/1972 | Knox | 206/365 |
| 3,705,788 | 12/1972 | Kolko et al. | 23/259 |

OTHER PUBLICATIONS

Sherwood Medical Industries, Inc. "Monoject Sterile-Disposable Syringes and Needles," 1970, pp. 1, 6, 7 and 9.
Sherwood Medical Industries Inc. "Monodose for the Hospital Pharmacy," 1971, pp. 1, 3, 6 and 7.

Primary Examiner—James T. McCall
Assistant Examiner—Robert W. Gibson, Jr.
Attorney, Agent, or Firm—Stanley N. Garber; William R. O'Meara

[57] ABSTRACT

A syringe tray having a plurality of circumferentially spaced sockets for frictionally receiving the needle sheaths of syringes. The sockets have longitudinal slots so that each sheath can be pivoted about a distal end portion thereof and moved through the slot to position the sheath and syringe associated with it at a selected angle relative to the tray.

14 Claims, 7 Drawing Figures

SYRINGE TRAY

DESCRIPTION

TECHNICAL FIELD

This invention relates to medical trays and more particularly to trays for holding a plurality of medical syringes.

BACKGROUND ART

In intradermal allergy testing, for example, a relatively large number of hypodermic syringes are generally used to intradermally inject a number of different allergens or antigens into different areas of a patient's skin. The allergist then reads the skin reaction to determine if any allergic reaction has occurred. So that the substance causing any allergic skin reaction in a given area of the skin will be known, it is convenient to use a known sequence of injections in a known sequence of skin areas.

In general, trays of various types for holding a plurality of syringes are known. For example, in some cases, a plastic tray is formed with a plurality of horizontal grooves which resiliently hold syringe barrels in place. Some trays have grooves for receiving syringes and for holding them under only limited tray tipping conditions. With some trays, each syringe is picked up with its needle sheath attached and then, generally with both hands, the sheath is removed to expose the needle. The sheath is held or placed on a table or other surface so that after use the sheath can be replaced over the used needle. Such handling of the syringe and sheath generally complicates the use of the syringe and increases the amount of time required to use the syringe. Also, if each syringe is placed back into the tray, the same syringe may be inadvertently picked up a second time.

DISCLOSURE OF INVENTION

The present invention is directed to overcoming one or more of the problems as set forth above and has an object to provide an improved syringe tray which simplifies the use of syringes carried by the tray.

In accordance with the present invention, a tray is provided which has a plurality of sockets for receiving and holding the needle sheaths of a plurality of syringes. The sockets have a slot which permits the sheath to be pivoted about its distal end so that the strength can be moved in the slot to position the syringe in an angular position relative to the tray. The syringe can be removed from the sheath and tray with one hand while the sheath remains in the tray socket. After use, the syringe needle can be inserted back into its needle sheath on the tray. If desired, the used syringe can be placed in some position angularly different from the position of the syringes not previously used so as to provide an obvious indication that a used syringe has been used.

An improved method of using a plurality of syringes in a preselected order is also disclosed.

BEST MODE FOR CARRYING OUT THE INVENTION

Figure 1:
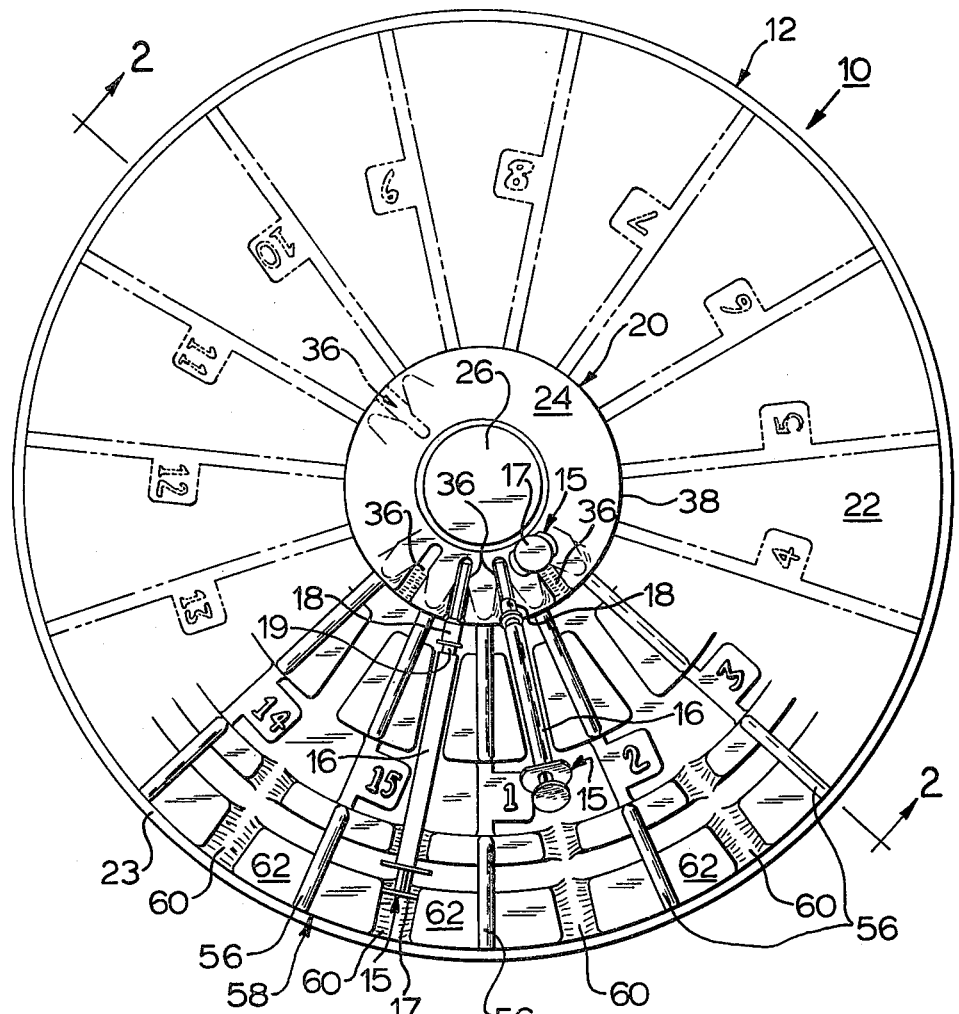
FIG. 1 is a top plan view, with some detail in phantom, of a syringe tray in accordance with a preferred embodiment of the present invention.
Figure 2:
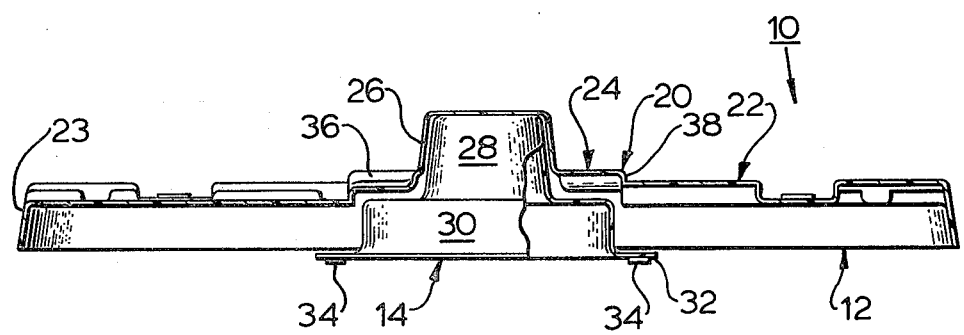
FIG. 2 is a cross-sectional view taken along the line 2—2 of FIG. 1.

Referring now to the drawings and particularly to FIGS. 1 and 2, a syringe tray assembly 10 is shown including a tray body member 12 disposed on a tray stand 14 for rotation. In FIG. 1, three hypodermic syringes 15 are shown on the tray 12 although a total of 15 syringes can be used with the tray 12 of the illustrated embodiment. Each syringe 15 includes a barrel 16, piston 17 and sheath 18 covering the syringe needle cannula (not shown) and frictionally connected to the barrel tip 19.

The tray 12 is preferably thermoformed of a suitable plastic, such as polystyrene. The supporting stand 14 may also be made of a suitable plastic such as polystyrene.

Tray 12 is a single-piece wheel or disc-shaped member and includes a central hub 20, a circular deck or a platform 22 that is integral with hub 20 and an outer peripheral depending skirt or wall 23. Hub 20 has a circular base portion 24 and a central upstanding portion 26 extending vertically from the base portion.

The stand 14 includes an upwardly extending center post 28 which is received in the vertically extending hub portion 26 (FIG. 2), and a circular base portion 30 of less height surrounding the post 28. The base 30 has a surrounding radially outer flange 32 which is adapted to engage a supporting surface. The flange 32 may be provided with several pads 34, for example, of the type which have an adhesive bottom surface after removal of a paper covering. In this way, the base or stand 14 may be adhesively positioned in a desired area and the tray 12 placed on top of the stand, such as illustrated in FIG. 2.

Referring now also to FIGS. 3-8, the base portion 24 of hub 20 is provided with a plurality of like grooves or slotted sockets 36 which extend radially outwardly from the central hub portion 26 to the radially outer circular end wall, indicated at 38, of the hub base portion 24. The sockets 36 are adapted to receive the needle sheaths 18 of the syringes. Each socket 36 has a radially outer entrance opening 40 (FIGS. 3 and 4) in the hub end wall 38. The radially inner end of each socket 36 is shown closed by an end wall 42. Each socket 36 has a longitudinal slot 44 in its upper wall which extends radially from the radially inner socket end wall 42 to hub end wall 38.

Figure 3:
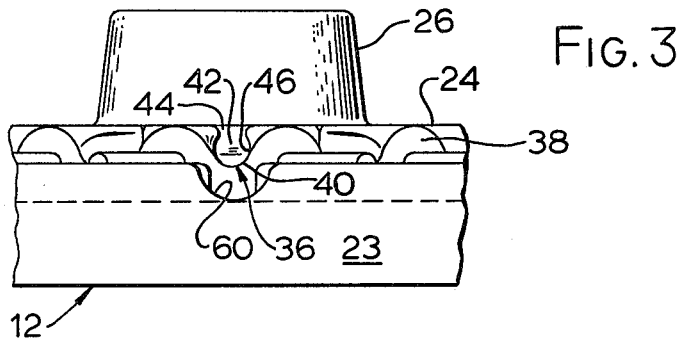
FIG. 3 is a fragmentary side view on an enlarged scale of the tray of FIG. 1.
Figure 5:
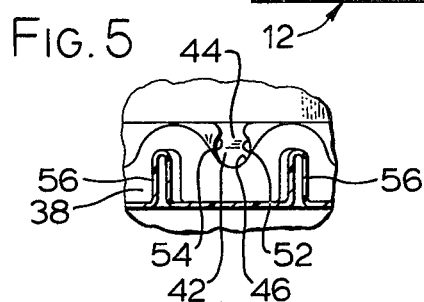
FIG. 5 is a cross-sectional view taken along the line 5—5 of FIG. 4.
Figure 8:
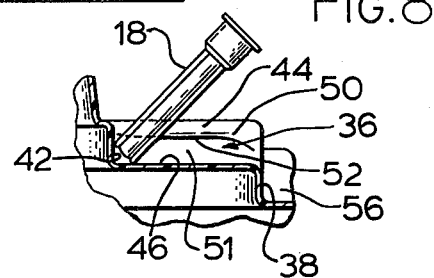
FIG. 8 is a cross-sectional view taken along the line 8—8 of FIG. 7.
Figure 4:
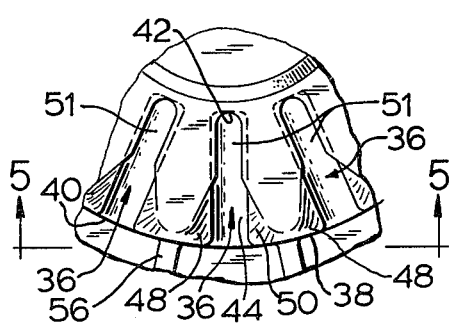
FIG. 4 is a fragmentary top plan view on an enlarged scale of the tray of FIG. 1.

The slot 44 is relatively wide at its radially outer end and relatively straight and narrow at its radially inner end. In the illustrated embodiment, each of the slotted sockets 36 has generally arcuate sidewall 46, as indicated in FIGS. 3, 5 and 8, but with opposed upper portions of the sidewalls adjacent the hub end wall 38 substantially flat and inclined upwardly and outwardly as indicated at 48 and 50. The inclined walls 48 and 50 tend to guide or facilitate the entrance of a needle sheath 18 into a socket 36. For example, a needle sheath 18 can be pressed downwardly between the walls 48 and 50 and then moved longitudinally into a radially inner portion 51 of each socket 36. The hub inner portion 51 of each socket has opposed upper sidewall portions 52 and 54 which extend arcuately toward each other. The width of the slot 44 shown at the inner portion 51 of the socket is less than the maximum width or diameter of the inner portion 51 for about one-half the length of the socket.

The deck 22 is shown divided by radial ribs 56 into wedge-shaped areas or zones between adjacent ribs. In the illustrated embodiment, tray 12 is divided into 15 zones which are numbered 1 through 15, for example, by molded numbers in a selected area of each zone. The ribs 56, as well as other channels and abutments shown, add strength to the tray so that even though the tray may be formed of relatively thin thermoplastic material, it has sufficient strength for its intended purpose. Each of the wedge-shaped zones contains a channel 60 aligned with a socket 36 and which are adapted to receive portions of the syringes when in horizontal positions on the tray 12. The channels are shown centered in each zone so that the number of the zone and the syringe disposed in that zone is readily ascertained. Various flat areas, such as indicated at 62 in FIG. 1, can be used to write on, for example, the allergen in the syringe of each zone and the patient's name may be placed on the tray 12.

Figure 6:
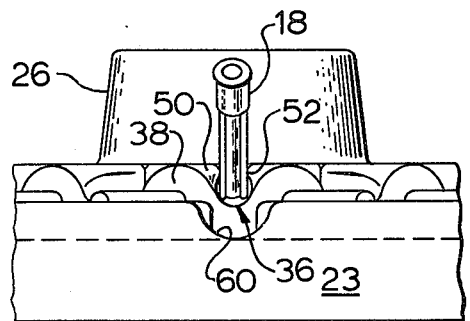
FIG. 6 is a fragmentary side view on an enlarged scale of FIG. 1 along with a needle sheath disposed in one of the sockets.
Figure 7:
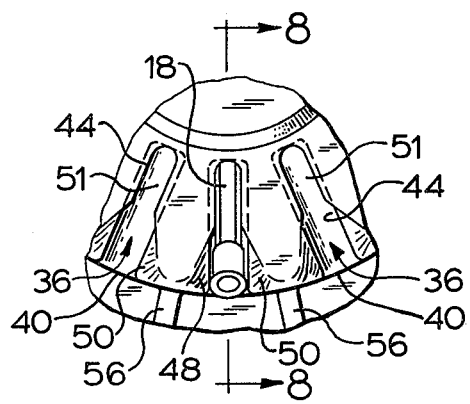
FIG. 7 is a fragmentary top plan view on an enlarged scale of the tray of FIG. 1 with a needle sheath in one of the sockets.

In FIG. 1, the three syringes 15 are shown, left to right, respectively, horizontally, at 45° and vertically at 90°, all relative to the plane of the tray. By "plane of the tray" is meant a plane normal to the vertical axis of rotation of the tray. In FIGS. 6-8, a sheath without the syringe is shown in a socket and extending at 45° to the tray.

The diameter or maximum width of socket portion 51 is approximately equal to or preferably slightly less than the diameter or width of the main portion of a sheath 18 so that the sheath, when horizontally disposed in a socket 36, is resiliently and frictionally held in place due to the resilience of the walls of the socket. Each sheath 18 and syringe can be moved from the horizontal position (syringe in zone 15) to an angular position (e.g. syringes in zones 1 and so 2) by lifting the proximal end of the syringe and that the sheath pivots on its distal end with the sheath moving upwardly and along the slot 44 of the socket. The syringe and sheath can be angularly moved so that they are positioned in the vertical position such as shown by the position of the syringe in zone 2. The opposed side walls indicated at 52 and 54 of the socket 36 resiliently and frictionally engage portions of the sheath so that the sheath will be maintained in a desired selected position at any angle relative to the plane of the tray between the horizontal position and the vertical position, that is, at any angle between 0° and about 90°.

In using the tray assembly 10 for intradermally injecting a number of different allergens into areas of the skin of a patient for determining allergic reactions, a plurality of sheathed syringes 15, for example, 15 syringes, are filled with selected allergens and then re-sheathed. The syringes are then placed in the respective zones by grasping each sheath and sliding it radially into a socket 36. Several such syringe trays 12 may be provided with filled syringes stacked one upon the other and stored for ready use, the syringes being stored generally in a horizontal position on each tray.

The tray may be removed from storage and placed onto the base 14 near the location where the injections are to take place. The tray can be rotated on stand 14 as the syringes are used to effect easy access to the unused syringes. Where desired, each syringe may be lifted by raising the proximal end of the syringe to some appropriate angle such as 30° or 45° as desired. For example, each syringe may be lifted to a 30° angle just prior to its use or all of the syringes may be lifted to such an angle prior to use for easy removal of each syringe. A syringe may be removed from the tray by grasping the syringe barrel and then, using the enlarged proximal end of the sheath 18 for leverage, pulling the syringe straight out of the needle sheath while maintaining the sheath in an angled position in the socket, such as illustrated in FIGS. 6, 7 and 8. After a syringe has been used to inject an allergen, the syringe is then returned to its sheath by inserting the needle into the sheath until the syringe tip 19 is frictionally received in the sheath. Where all of the syringes were originally placed in an angular raised position before use, the syringe after use may desirably be flattened or pushed downwardly to a horizontal position so that it will be apparent that that particular syringe has already been used. As the syringes are used to inject an allergen and then returned to the tray by re-sheathing them, the tray may be rotated, as previously mentioned, to bring the next syringe to be used adjacent to the person using the syringe so as to decrease the reach needed.

The syringes are preferably used in succession and the areas of skin injected used in a successive or predetermined manner so that, at any time, a person seeing a reaction in a given area of the skin will know which syringe was used and therefore the allergen causing the reaction.

If desired instead of raising all of the syringes prior to use, the syringes could be picked up and removed one at a time and from the horizontal position. In such case, when the syringe is returned to the tray by re-sheathing it, it can be maintained at some angle between the horizontal and vertical to provide an indication that the syringe has been used. After the syringes have all been used, they may be taken to a disposal area for destruction and disposal.

By being able to raise and lower syringes angularly while they remain sheathed and in the desired position, the syringes are easily and quickly removed and replaced on the tray, and there is less chance of error since the used sheaths may be positioned at an angle different from those syringes which have not as yet been used. Each syringe can be conveniently removed from the tray by one hand. Since the sheaths are frictionally held in the cylindrical slot portion of the socket, the tray can be transported and bumped without danger of the syringes falling off the tray. Also, syringes of different capacities or lengths can also be used with the tray assembly 10. In the illustrated embodiment, each syringe barrel on the tray 12 is frictionally connected with its sheath because the barrel tip is frictionally received into the proximal end of the sheath but the barrel and plunger are not otherwise resiliently and frictionally engaged and held by the tray 12. In this way, each syringe barrel is readily grasped and angularly moved, and is easily removed from its sheath when desired.

As various changes could be made in the above construction without departing from the scope of the inven-

I claim:

1. A tray for holding a plurality of syringes having needle sheaths thereon comprising a tray body including a hub having a plurality of spaced longitudinally extending sockets disposed in a portion of said hub in a circular array with their longitudinal axes extending radially, each of said sockets having an end opening for receiving the distal end of a sheath when the sheath is inserted longitudinally into a socket, and a slot in the sidewall of the socket extending longitudinally from said opening to permit the sheath to extend from the socket and through the slot in angular relation to the longitudinal axis of the socket.

2. The tray of claim 1 wherein the outer periphery of said tray body is circular.

3. The tray of claim 1 further including a stand having a portion thereon for supporting said tray body for rotation relative to said stand.

4. A tray for holding a plurality of syringes having needle sheaths disposed on distal portions of the syringes comprising a generally disc-shaped tray body having an axial hub including a central vertically extending portion, a base portion surrounding said vertically extending portion, and a plurality of radially extending, circumferentially spaced sockets in said base portion, each of said sockets having an end opening and a radial slot in the upper wall of the socket extending longitudinally of the socket, each of said sockets having a radially inner portion having a maximum width dimension greater than the width of the slot of said radially inner portion of the socket whereby a needle sheath is longitudinally insertable through one of said socket openings into said one socket and is pivotal about the distal end of the sheath and movable through the slot to position the sheath at a selected angle relative to the plane of the tray with the opposed walls of the slot in said radially inner portion resiliently and frictionally engaging the sheath.

5. The tray of claim 4 wherein a sheath when in a socket is movable angularly with respect to the plane of the tray through about 90°.

6. The tray of claim 5 wherein said tray body is of a plastic material.

7. The tray of claim 4 or 6 wherein said tray body includes a generally circular deck portion integral with said hub for supporting portions of syringes when the sheaths of the syringes are disposed in said sockets with the longitudinal axes of the syringes parallel to the plane of the tray.

8. The tray of claim 4 further including a stand having an upstanding portion receivable in the hub of said tray body to support the same for rotation relative to said stand.

9. In combination with the tray of claim 4, of a plurality of hypodermic syringes each having a needle sheath covering the needle of the syringe, each of said sheaths having an outer dimension capable of insertion longitudinally through a socket opening and into the socket and pivotal on the distal tip portion of the sheath and movable through the slot to position the syringe at an angle to the plane of the tray.

10. A syringe tray for holding a plurality of syringes comprising a single-piece plastic, generally disc-shaped tray body having a vertically extending hub in the center of said body, a plurality of sockets arranged in circumferentially spaced relation around said hub, each of said sockets having a longitudinal axis extending radially and having an opening to the socket at the radially outer end of the socket, each of said sockets having a longitudinally extending slot extending radially from the socket opening to a wall at the radially inner end of the socket, and a radially inner socket portion, said body having a circular deck surrounding and integral with said hub, said deck having wedge-shaped zones extending in a circumferential array around said hub and each having a channel in aligned relation with one of said sockets, a portion of each of said slots in said radially inner socket portion having a width less than the maximum width of the socket so that a sheath when extending through a socket at an angle to the plane of said tray body is frictionally engaged by the opposed sides of the socket slot in said radially inner socket portion for holding said syringe at said angle.

11. The tray of claim 10 further including a stand having an upstanding post receivable within said hub for permitting rotation of said tray body relative to said stand.

12. The tray of claim 12 wherein each of said sockets has opposed walls outwardly angled adjacent the socket opening to facilitate insertion of a sheath into the socket.

13. In combination with the tray of claim 10 of a plurality of syringes each having a barrel, a piston in the barrel, a needle and a sheath covering said needle and frictionally connected to the to the distal end portion of the barrel, each of said sheaths being insertable into one of said sockets, each of said syringes being pivotal on the distal end portion of its sheath when the proximal end of the syringe connected thereto is lifted whereby said sheath moves through a portion of the socket slot and angularly to the plane of said tray body, each of said sheaths having a width slightly greater than the width of a portion of the socket slot so as to be frictionally held by the walls of the slot when in a selected angular position.

14. The combination of claim 13 wherein said tray body is formed of a thermoplastic and has an outer peripheral circular depending wall.

* * * * *